United States Patent [19]

Bernstein et al.

[11] 4,284,444

[45] Aug. 18, 1981

[54] ACTIVATED POLYMER MATERIALS AND PROCESS FOR MAKING SAME

[75] Inventors: Bruce S. Bernstein, Somerville, N.J.; Seymour Hyman, New York, N.Y.; Ramesh C. Kapoor, Seaford, Del.

[73] Assignee: Herculite Protective Fabrics Corporation, New York, N.Y.

[21] Appl. No.: 32,593

[22] Filed: Apr. 23, 1979

Related U.S. Application Data

[60] Continuation of Ser. No. 821,045, Aug. 1, 1977, abandoned, which is a continuation of Ser. No. 255,282, May 19, 1972, abandoned, which is a division of Ser. No. 112,053, Feb. 2, 1971, Pat. No. 3,705,938, which is a continuation-in-part of Ser. No. 593,267, Nov. 10, 1966, abandoned.

[51] Int. Cl.³ .................. B32B 31/04; B32B 31/12; B32B 31/30
[52] U.S. Cl. ................... 156/60; 156/242; 156/244.11; 156/308.2; 264/175; 264/176 R; 264/212; 264/215; 264/216; 427/180; 427/384; 427/384.4; 427/393; 427/397; 427/421; 427/430.1
[58] Field of Search ............ 156/306, 71, 308.2, 156/60, 242, 244.11; 428/96, 515, 921, 922, 245, 246, 265, 286, 297, 480, 343, 354, 220, 518; 239/34, 54; 427/180, 384, 389.9, 393, 397, 421, 430.1; 424/21, 19, 16, 32, 33, 178, 81; 260/DIG. 15, DIG. 21; 264/175, 176 R, 212, 215, 216

[56] References Cited

U.S. PATENT DOCUMENTS

| | | | |
|---|---|---|---|
| 2,497,045 | 2/1950 | Killingsworth | 260/33.6 |
| 2,991,193 | 7/1961 | Fessler et al. | 428/335 |
| 3,279,986 | 10/1966 | Hyman | 424/27 |
| 3,288,669 | 11/1966 | Hechenbeikner | 424/288 |
| 3,446,651 | 5/1969 | Clachan et al. | |
| 3,508,944 | 4/1970 | Henderson et al. | 264/95 |
| 3,565,836 | 2/1971 | Fuller | 260/31.8 |
| 3,578,545 | 5/1971 | Carson et al. | |

OTHER PUBLICATIONS

F. W. Billmeyer, Jr. Textbook of Polymer Science, second edition 1962, John Wiley & Sons, pp. 3,517 & 530.

Modern Plastics Encyclopedia, Oct. 1976 vol. 53, No. 10A pp.482–485, McGraw Hill Inc., New York, NY.

*Primary Examiner*—Stanley S. Silverman
*Attorney, Agent, or Firm*—Sughrue, Mion, Zinn, Macpeak and Seas

[57] ABSTRACT

This invention concerns non-porous, polymeric articles having active properties, and methods for producing such articles. Plastic, rubber, or other natural and synthetic polymeric articles are provided with active chemical and/or physical properties, such as, antibacterial, antifungal, pesticidal, insecticidal, animal repellent, odorous, antistatic, electrically conductive or other properties or combinations of properties, by applying to a surface of the article selected activating agents which are capable of migrating or moving throughout the body of the article to impart an effective level of activity throughout the article and/or on a surface other than the one to which the activating agents have been applied.

37 Claims, No Drawings

ACTIVATED POLYMER MATERIALS AND PROCESS FOR MAKING SAME

RELATED APPLICATIONS

This application is a continuation of application Ser. No. 821,045, filed Aug. 1, 1977 now abandoned, which is a continuation of Ser. No. 255,282, filed May 19, 1972 and now abandoned, which is in turn a divisional application of Ser. No. 112,053, filed Feb. 2, 1971 and now U.S. Pat. No. 3,705,938 which is in turn a Continuation-in-Part of U.S. Ser. No. 593,267 filed Nov. 10, 1965, now abandoned.

BACKGROUND OF THE INVENTION

1. Field of the Invention

The present invention relates to non-porous, natural and synthetic polymeric articles having chemical and/or physical or other active properties or combinations of properties. The invention also relates to methods for preparing such articles.

More specifically, the invention relates to polymeric articles havng active properties and to the manufacture of such articles by applying to a surface of the article selected activating agents which are capable, in migrating or moving throughout the body of the article, of imparting an effective level of activity throughout the article and/or on a surface other than the one to which the activating agents have been applied.

2. Description of the Prior Art

It is known in the art that active properties can be imparted to polymeric articles by a variety of methods. One common method is to incorporate one or more activating agents into the polymeric compound during the mixing or blending phase prior to processing or manufacturing the article. Activation is accomplished by thoroughly distributing the activating agents throughout the compounding ingredients. For example, synthetic thermoplastics, natural and synthetic rubbers and other polymeric materials have been blended with activating agents such as, antibacterial, antistatic, electrically conductive and other chemically or physically active agents. The activated polymeric materials are then formed into sheets, fibers, rods or other configurations by molding, casting, extruding, calendering and/or other manufacturing or processing operations.

This method has many shortcomings. Often, certain active properties cannot be obtained, as when the presence of the activating agents in the polymeric compound causes difficulties during the processing, shaping and/or finishing of the article. In calendering, for example, the presence of the active ingredient often makes it difficult to attain an integral film. Activating agents which decompose or volatilize at the processing temperatures normally required for calendering cannot be incorporated in the pre-mix compound. Also, activating agents producing toxic vapors during processing require expensive manufacturing procedures, controls and equipment.

Another serious shortcoming of this method is that components, such as polymeric film used in laminates, must be produced with the activating agents incorporated in them prior to conversion to the finished article. When similar articles are made from active and inactive components, such as laminates made from active and inactive calendered polymeric film, the films must be kept in stock in both active and inactive grades. If various types of activity are desired, stocks must be maintained having each type of activity, which is an expensive procedure.

A second method widely used to impart certain active properties to the exposed or working surface is to apply a compound containing active agents to that surface. For example, anti-fouling marine paints, antifungal sprays and coatings, fire resistant coatings and antistatic coatings have been applied to the surface of the article. The activity of such coatings is superficially "skin deep" and surface activity is lost to the extent that the activated coating peels or is mechanically abraded, chipped or washed away from the inactive substrate. While this method affords certain flexibility in providing an activated surface, it is at best subject to limitations of available range of active ingredients that can be applied in this manner—plus limited service life and efficiency.

Another method for the production of activated articles is to expose the article to the vapors of a volatilized chemical. This ancient technique has long been applied to textiles, polymer sheets, or the like and comprises vaporizing a volatile agent, usually a biologically active agent, and then exposing the textile or other article to the vapors. A major disadvantage of this method, however, is that it requires special buildings, ventilation and recovery equipment, and safety procedures. Since the active agent has a volatilization temperature which necessarily is much lower than the melting point of the article to which the activating vapors are applied, the activation may be readily lost where the article is exposed to elevated temperatures. Thus, the treated material may be rapidly deactivated when subjected to wet or dry heat, for example, by exposure to steam sterilization or other high temperature washing procedure, intense sunlight, etc.

An important object of this invention, therefore, is to overcome the disadvantages of the prior art by providing a method for activating non-porous polymeric articles by applying the activating agents to one surface of the article so that the agents migrate throughout the body of the article and impart an effective level of activity throughout the article and on surfaces to which the activating agent has not been applied. The articles made by this method comprise an active layer which is applied on one surface of the article, and which contains an active migrating agent. The concentration of the agent is in excess of the concentration needed to provide an effective level of activity in the layer, and is sufficient, upon migration of the agent from the layer, to impart an effective level of activity throughout the entire article. The high concentration of the active migrating agent in the layer also provides a reservoir of activating material capable of replenishing the effective surface activity of the article.

The methods and products of this invention do not require extreme processing conditions so that volatile activating agents are conveniently used at normal temperatures; toxic agents can be handled safely; and a wide variety of inactive polymers can be given almost any desired activation. Only stocks of inactive articles are needed and the desired activation may be applied when desired. The activated article has long lasting properties which persist even if a surface layer is removed and which are replenished from the reservoir of activating agent contained within the active layer.

Disclosures of procedures representative of the prior art known to applicants are to be found in the U.S. Pat.

Nos. 359,166, Mathieu, issued Mar. 8, 1887; 2,272,397, Becher, issued Feb. 10, 1942; 2,770,566, Ritter, issued Nov. 13, 1956; 2,785,106, Mendelsohn, issued Mar. 12, 1957; 2,919,200, Dubin et al, issued Dec. 29, 1959; 2,933,401, Schmitz-Hellebrecht, issued Apr. 19, 1960; 3,096,183, Geuth, issued July 2, 1963; 3,247,058, Hyman, issued Apr. 19, 1966; 3,279,986, Hyman, issued Oct. 18, 1966; 3,288,669, Heckenbleikner, issued Nov. 29, 1966; and 3,308,488, Schoonman, issued Mar. 14, 1967.

THE INVENTION IN BRIEF

This invention generally comprises the production of nonporous, polymeric articles having active properties by applying to the surface of a preformed polymeric article a layer containing a selected activating agent which is capable of migrating through the body of the polymeric article to impart active properties throughout the article and/or on surfaces not contacted by the layer.

Specifically, the present invention concerns the introduction of chemically and physically active properties into a preformed article of non-porous polymeric material. The active properties which are introduced into the polymeric article include, but are not limited to, chemical properties, such as, biological properties, for example, antibacterial, antifungal, odorous, pesticidal, repellent and insecticidal properties, and physical properties, such as, electrically conductive, and antistatic properties, and combinations of such active chemical and physical properties.

DETAILED DESCRIPTION OF THE INVENTION

The invention may be applied to any non-porous polymeric article, regardless of the shape or configuration of the article, or the process by which the article is formed.

The activated article may be in any form, for example, single sheets or multi-ply laminates, films, rods, fibers, woven and non-woven fabrics, etc., and the article may have been produced by any molding, shaping or fabicating method, such as, casting, extrusion, calendering, or any other conventional forming process.

The non-porous, polymeric articles to which the invention may be applied comprise any natural or synthetic material, including any natural or synthetic thermoplastic or thermosetting polymer.

Articles of polymeric materials, used to protect man and his possessions from the environment may be made by the present invention. Activated polymeric articles, whether reinforced, or combined with other materials, are especially suited to production by the present method. Items which can be produced by the present method include protective coverings for equipment, livestock and materials, protective clothing, mattress ticking, hospital, hotel, motel, school fabrics, upholstery, wall coverings, curtains, packaging tubing, floor tiles, floor coverings, plastic laminated furniture, countertops, plastic clad metals, liners and coverings for food processing equipment and installations.

The invention is particularly useful in the production of activated polymeric articles in the form of rigid or flexible sheets or films, in single or multi-ply products, including laminates incorporating a rigid substrate or flexible scrim or other woven or non-woven reinforcing, backing or facing components.

The activating agents may be applied in solid or liquid form by any suitable procedure. The activating agent may be applied and maintained as a liquid encapsulated between plies of a laminate or may be set or hardened to solid form. The activating agent may be applied as a solid, such as, a preformed layer or as a layer of discrete particles. Depending on the characteristics of the activating agent, it can be conveniently dissolved or dispersed in a solvent or carrier vehicle which is then applied to the surface of the polymeric substrate, or it may be applied directly without a solvent, binder or carrier vehicle, or the like.

More specifically, in many instances it is convenient to apply the active agent as a solution in a volatile solvent; a solution or dispersion in a liquid vehicle composed of a resin binder in an aqueous or other emulsion; a solution or dispersion of the active agent in a 100% solids vehicle; or a solution or dispersion in a combination of vehicles including solutions, emulsions and 100% solids vehicles. The necessary condition is that the active agent be applied in conjunction with a medium through which the agent can effectively migrate to reach the article to be activated.

Any procedure, such as, coating, spraying, dipping, immersion, printing, dusting, or sheet-to-sheet bonding or laminating may be utilized to achieve the necessary contact between the activating agent and the polymeric substrate, so that an effective level of activation may be imparted to the polymeric article. The process does not depend upon specific temperatures, pressures, and contact times, and may be effected under ambient conditions or under elevated temperature and/or pressure, depending on the method employed. Most activating agents impart effective activity throughout the article within approximately one week. Some activating agents may impart effective activity more quickly, while others may take a somewhat longer period of time to impart an effective level of activity. Many active agents will not perform in accordance with this invention and thus will not impart effective activity, no matter what the length of contact time.

As noted above, the invention may be utilized to produce polymers having chemical activity, including but not limited to biological activities, such as antibacterial, antifungal, pesticidal, insecticidal, animal repellent and odorous properties; and physical activity, including but not limited to antistatic and electrically conductive properties.

One embodiment of the present invention relates to a process for producing biologically active, e.g., antibacterial, polymeric materials and to the resulting products. Specifically, this aspect of the invention relates to antibacterial materials incorporating a body of non-porous polymer, such as, one or more films of plastic.

Various fibers, fabrics and combinations thereof having antibacterial activity are well known. Such products have been widely used in hospitals, laboratories, shops, homes, and in the outdoors as protective covers, mattress and pillow ticking and covers, wall coverings, etc. Most of these articles are often repeatedly subjected to high temperature washing operations and tend to lose their antibacterial activity over the period of use.

This embodiment provides a process for producing antibacterial polymeric articles, such as, plastic sheet materials in which the antibacterial properties are present throughout the entire body of the material, and also provides improved antibacterial plastic sheet or other polymeric materials having superior resistance to loss of activity during washing and laundering.

By way of illustration, the method of this invention may be practiced in the field of biologically active materials by providing a substrate of a non-porous polymeric article, such as a plastic sheet, and applying to one surface of the sheet a polymeric liquid composition which contains a selected antibacterial agent which migrates throughout the body of the plastic sheet and imparts an effective level of antibacterial activity on the surface of the sheet opposite to the surface to which the active polymeric liquid composition has been applied.

This antibacterial activity is effective against bacteria, including both gram positive and gram negative organisms.

The active polymeric liquid composition may then be set to form a solid film on the surface of the plastic sheet. As a result, the product exhibits effective antibacterial activity on both surfaces and throughout the body of the plastic sheet.

In an especially preferred embodiment of the invention, an activated polymeric liquid composition is introduced as a core layer between outer plies of flexible sheets of polymeric material, at least one of which is a flexible sheet of non-porous polymeric material. After setting of the polymeric liquid composition as a core layer to form a solid laminated product, the migration of the antibacterial agent from the core through the outer ply of non-porous polymeric material is found to have imparted an effective level of antibacterial activity to the outer surface of the ply.

In the manufacture of laminated materials, as above described, very valuable commercial materials are obtained by using two outer plies of non-porous, polymeric sheet material, such as, flexible polyvinyl chloride sheets or films, and by reinforcing the structure with a textile element between the outer plies to provide an especially tough, durable and abrasion resistant material.

In practicing the invention with respect to single or multi-ply polymer sheet applications, there may be used as the sheet of polymer, any polymeric material which is capable of being formed into a self-supporting continuous sheet or film, having adequate mechanical properties to withstand normal handling, abrasion, etc. The polymeric material in sheet form must be substantially non-porous. Suitable materials include various hydrocarbon polymers, such as, rubber, and olefins, for example, polyethylene and polypropylene, imide, amide, ester, urethane, carbonate, cellulosic, halocarbon, ionomer, vinyl, such as polyvinyl chloride, polyvinylidene chloride, polyvinyl acetate, and other polymers, and their blends, interpolymers and copolymers.

Polyvinyl chloride films are especially useful in the invention. While thickness of the sheet material is not critical, and articles of around 0.100 inches thick can be produced, excellent results have been obtained with single sheets having a thickness of about 0.015 inches, and with multi-ply laminates having a combined thickness of about 0.030 inches.

The polymeric liquid composition which is applied to the surface of the polymer substrate, in accordance with one embodiment of the invention, may include any liquid composition capable of being set to form a solid film of plastic on the surface of the base sheet. Thus, the term should be understood to include plastisols, polymer solutions, polymer-in-liquid emulsions, and 100% solids liquid polymers.

As the antibacterial agent, there may be employed any antibacterial material capable of being carried in the polymeric liquid composition and capable of migrating through the polymer base sheet.

Where a reinforcing element of closely woven, loosely woven or non-woven textile is employed in the production of laminated products, any suitable fiber, such as, cotton, nylon, polyester, fiber glass or other fibers, may be employed.

Where flexible or rigid laminated materials are prepared, the polymeric liquid composition is preferably a plastisol or other adhesive which bonds together outer plies of the non-porous, polymeric sheets and may also bond the outer plies to rigid substrates, such as wood or metal, or to flexible substrates, such as reinforcing fabrics, for example, a nylon scrim or other textile fabric. Laminates may also be formed by bonding a single ply of the non-porous polymer to a layer of reinforcing material by means of the plastisol adhesive. For example, a particle board or other rigid substrates may be surfaced with a nonporous polymeric film, such as wood grain printed polyvinylchloride using an adhesive containing an antibacterial activating agent which migrates through the polymeric film to impart effective antibacterial activity to the outer surfaces. Such products may be used as counter tops or furniture components in hospitals, bathrooms and other areas requiring these properties.

The invention as applied to biologically active products will be more fully appreciated in the light of the following examples. In connection with these examples, certain tests were employed to evaluate the effectiveness of the method of the invention in imparting active properties to inactive polymeric article.

Description of Test Method

In the evaluation of the invention relative to antibacterial effectiveness, the following four tests were employed:

(A) NYS-63 Antibacterial Test Method

1. Test bacteria were transferred daily in American Association of Textile Chemists and Colorists (AATCC) Bacteriostasis Broth containing 5% dextrose. A 0.01 ml sample of a 24 hour broth culture was transferred and incubated at 37° C.

2. Culture media used in the tests were of the following compositions:

| (a) | AATCC Broth: | | |
|---|---|---|---|
| | Peptone | 10 | g |
| | Sodium Chloride | 5 | g |
| | Beef Extract | 5 | g |
| | Distilled Water | 1000 | g |
| (b) | Letheen Broth: | | |
| | Part I | | |
| | Lecithin (azolectin) | 0.7 | g |
| | Sorbitan Monoleate (Tween 80) | 5.0 | g |
| | Distilled Water | 400 | ml |
| | Part II | | |
| | Peptone | 10 | g |
| | Sodium Chloride | 5 | g |
| | Beef Extract | 5 | g |
| | Distilled Water | 600 | ml |

Dissolve the Lecithin and Tween 80 in 400 ml of hot distilled water and boil until clear; add Part II and boil ten minutes; adjust the volume to 1000 ml; adjust the pH to 7.0+0.2 with N/1 NaOH and/or N/1 HCl filter through coarse filter paper, dispense and sterilize at 15 lb. steam pressure for 20 minutes.

3. The AATCC Agar used in the tests was of the following composition:

| Peptone | 10 g |
|---|---|
| Sodium Chloride | 5 g |
| Beef Extract | 5 g |
| Agar agar | 15 g |
| Distilled Water | 1000 ml |

4. The antibacterial test procedure was as follows:

(a) Size of Inoculum Per Sample

The inoculum should contain sufficient organisms in AATCC bacteriostasis broth. The dilution should be made from a 24 hour broth culture in which the number of organisms per unit volume has been accurately and rapidly established by a suitable counting method.

(b) Size and Shape of Test Sample

Cut one square inch discs from the test material.

(c) Controls

Samples of control material containing no antibacterial agent shall be inoculated in the same manner as the test samples.

(d) Inoculation of Polymer

Two or three bottom sections of 35×10 mm. disposable tissue culture dishes (Falcon catalogue #1008) shall be placed in standard Petri dishes containing 10 ml. of sterile distilled water. Place 0.2 ml. of a 24 hour broth culture containing $10^5$ organisms in the center of each disposable tissue culture dish. The test and control discs shall then be placed in the disposable tissue culture dishes with treated surface in contact with the inoculum. The covers shall then be replaced on the standard Petri dishes. The latter shall be placed on a level shelf in an incubator at 37° C. This procedure provides for optimal growth of the bacteria at 100% relative humidity.

(e) Incubation

The samples shall be incubated at 37° C. for 24 hours.

(f) Sampling of Inoculated Swatches

After incubation for the prescribed periods, the disposable tissue culture dishes containing the sample shall be removed from the Petri dish by means of a flamed forceps and placed into 50 ml. of letheen broth in an 8 oz. wide mouth jar. Shake vigorously for about one minute after sample and tissue culture dish are separated. Make serial dilutions and place in AATCC bacteriostasis agar.

(g) Incubate plates for 24 to 48 hours at 37° C.

(h) Calculate percentage reduction of the inoculum by treated samples vs. untreated samples.

(B) NYS-63 Modified Antibacterial Test-Tripticase Soy Broth is used instead of Letheen Broth.

(C) Agar Plate Method-AATCC Method 90-1965T (D) Modified Agar Plate Method-AATCC Test Method 90-1965T-Appendix A-1-(Seed Layer)

With reference to the NYS-63 tests for antibacterial activity, an effective level of such activity is considered to be one which gives at least 70% reduction in bacteria growth as compared with a control sample.

With respect to the Agar Plate Method and Modified Agar Plate Method tests for antibacterial activity, an effective level of such activity is judged by visual observation of a zone of inhibition of bacteria growth around a specimen. If there is any observable zone of inhibition around the specimen, the level of activity is judged to be effective.

In connection with the following group of examples in which antibacterial activity is evaluated by the foregoing test methods A-D inclusive, the evaluations were made with reference to the following bacteria:

(a) *S. Aureus* (gram positive) American Type Culture Collection No. 6538

(b) *E. Coli* (gram negative) American Type Culture Collection No. 4352

(c) *P. Aeruginosa* (gram negative) American Type Culture Collection No. 7700

(d) *B. Ammoniagenes* (gram positive) American Type Culture Collection No. 6871

(e) *P. Mirabilis* (gram negative) American Type Culture Collection No. 9921

(E) Fungistatic Test Method

In evaluating effectiveness of the invention to impart fungistatic properties to unactivated polymeric articles, the following test procedure was employed:

(a) Pour Nutrient-salts agar into sterile petri dish and let it solidify. The nutrient salts were prepared as described in ASTM D-1924-63 Test Method.

(b) Place test sample disc, along with a control, on top of agar.

(c) A piece of sterile filter paper, slightly smaller than the Petri dish, is then placed over the top of the test sample discs and the whole plate is then sprayed (from a sterile atomizer) with a prepared spore suspension of Chactomium Globosum, or other fungi spores.

(d) The dish is then covered with a lid and placed in the incubator at 28° C.-30° C. Results based on visual observation of inhibition are recorded at 7-day intervals for a total of 21 days.

(e) Growth above the test disc is compared with growth above the untreated control disc to determine effectiveness.

With reference to the antifungal test method the level of activity is determined by visual observation of the relative inhibition of fungal growth over a specimen, when compared with a control sample. The extent of fungal inhibition was graded as follows: total, high, moderate, low and no inhibition. The level of activity is considered effective where moderate or greater inhibition is observed.

Further, with respect to the following examples, a studied effort was made to demonstrate the efficacy of the invention as applied to systems comprising all of the common polymeric substrate materials and representatives of the major categories of biologically active chemical compounds. Thus, phenolic, metallo-organic, inorganic metal salt, organic sulfur, antibiotic, quaternary amine, carbonyl, carbocyclic and halogenated carbocyclic, and other biologically active compounds were successfully employed in accordance with the invention.

Not every biologically or otherwise active agent successfully migrates in each polymeric substrate to impart the desired level of activity and a certain amount of selection is required on the part of those practicing this invention. However, operable systems embodying all of the common commercial polymers and the recognized types of biologically active agents or other active agents have been demonstrated and other systems incorporating these and other metal materials will be seen to be feasible on the basis of this disclosure.

The primary subject matter of the various groups of specific examples may be summarized as follows:

Examples 1–7 and 10–12-Preparation of polyvinyl chloride articles having biological activity Example 13-Permanence of activity Examples 8–9 and 14–59 -Preparation of biologically active articles comprising various combinations of polymeric substrate and biologically active agent Examples 71—73-Preparation of textile fibers having biological activity Examples 77–87-Preparation of biologically active articles comprising multi-ply polymeric substrates Examples 69–70-Preparation of polymeric articles having odorous properties Examples 74–75-Preparation of polymeric articles having repellant properties Examples 90–97-Preparation of polymeric articles having antistatic properties.

In the following examples, the biologically active agents which have been utilized are identified as follows:

|  | Chemical Designation | Type |
| --- | --- | --- |
| Dowicide A | o-Phenylphenol, sodium salt | Phenolic |
| Metasol 57 | Phenylmercuric propionate | Metallo-organic |
| Arquad S-50 | Trimethyl soyammonium chloride | Quaternary Organic Salt |
| Captan | N-(trichloromethylthio)-4-cyclohexene-1,2-dicarboximide | Organic Sulfur |
| TBTSS | Bis(tri-n-butyltin)sulfosalicylate | Metallo-organic, Organic Sulfur |
| Mercuric chloride | Mercury bichloride | Inorganic Metal Salt |
| Paraformaldehyde | Trioxymethylene | Carbonyl |
| Tetracycline HCl | 4-(Dimethyl amino)-1,4,4a,5, 5a,6,11,12a-octa-hydro-3,6,10, 12,12a-penta-hydroxy-6-methyl-1, 11-dioxo-2-naphthacenecarboxamide hydrochloride | Antibiotic |
| BioMeT-14 | Diphenylstibine 2-ethyl hexoate | Metallo-Organic |
|  | Pyrethrins | Carbocyclic, Carbonyl |
|  | Piperonyl Butoxide | Synergistic with Pyrethrins |
| Hexachlorophene | 2,2'-Methylenebis 3,4,6-trichlorophenol | Phenolic |
| Hyamine 1622 | Diisobutylphenoxyethoxyethyl dimethyl benzyl ammonium chloride, monohydrate | Organic Salt |
| Hyamine 3500 | n-Alkyl dimethyl benzyl ammonium chloride | Quaternary Organic Salt |
| Metasol BT | Phenylmercuric borate | Metallo-organic |
| Chlordane | 1,2,4,5,6,7,8,8-Octachloro-3a, 4,7,7a-tetrahydro-4,7-methanoindan | Halogenated Carbocyclic |
| Fungitrol 11 | N-(trichloromethylthio)phthalimide | Organic Sulfur |
|  | Methyl nonyl ketone | Carbonyl |
|  | Tri-n-butyltin neodecanoate | Metallo-organic |
|  | 10,10'-oxybisphenoxyarsine | Metallo-organic |
|  | Copper-8-quinolinolate | Metallo-organic |
|  | Tri-n-butytin linoleate | Metallo-organic |
|  | Tri-n-butyltin monopropylene-glycol maleate | Metallo-organic |
|  | Tri-n-butyltin acetate | Metallo-organic |

EXAMPLE 1

There was provided a sheet of polyvinyl chloride film having a thickness of 0.00375 inches. One surface of the film was then coated with a plastisol coating containing about 3% by weight of the film of tri-n-butyltin neoderanoate as an antibacterial agent. The plastisol was prepared by dispersing 100 parts of polyvinyl chloride resin and about 8 parts of calcium carbonate in about 100 parts of dioctylphthalate and then dispersing 13.5 parts of tri-n-butyltin neodecanoate into 200 parts of plastisol. The plastisol was stirred until uniform and the coating was applied to the base sheet in a thickness of about 0.002 inches.

The antibacterial properties of the resulting product were then determined by the NYS-63 Method.

Control experiments were also performed concurrently and the percent reduction in growth in the presence of the antibacterial agent was observed. The tests of the material produced in accordance with this example showed that the uncoated side of the polyvinyl chloride film gave a 90% reduction in bacterial growth in comparison with the control material.

The coated side of the resulting material gave a 96% reduction in bacterial growth.

The amount of antibacterial agent employed in this and the following examples is sufficient to provide up to about 5% by weight of the combined weight of the inactive polymer layers, after drying of the liquid polymer composition.

EXAMPLE 2

A sheet of polyvinyl chloride film having a thickness of 0.013 inches was coated with a plastisol composition, as described in Example 1, but containing about 3%, based on total polyvinyl chloride film weight, of a solution of 10,10'-oxybisphenoxyarsine in epoxidized soybean oil as the antibacterial agent.

The coated polyvinyl chloride film was then overlayed with a piece of nylon scrim and a second sheet of polyvinyl chloride film, this one having a thickness of 0.00375 inches. The laminate was allowed to set under suitable conditions of heat and pressure until an integral, firmly bonded product was obtained.

Upon testing by the NYS-73 Method, it was found that the outer surface of 0.013 inches thick polyvinyl chloride film gave a 99.6% reduction and the outer surface of the 0.00375 inch polyvinyl chloride film a 99.7% reduction in bacterial growth when tested against S. Aureus, as compared with a control sample.

EXAMPLE 3

A fabric was prepared by coating a 0.00375 inch polyvinyl chloride film with a plastisol containing 100 parts polyvinyl chloride, 50 parts Kodaflex AD-2, a polymeric plasticizer, dioctylphthalate, Texanol isobutyrate, epoxidized soybean oil and a heat stabilizer and about 3% of the same antibacterial agent used in Example 2. The coated base sheet was then overlayed with a nylon scrim element and a sheet of 0.00375 inch polyvinyl chloride, and was allowed to set under suitable conditions of heat and pressure until an integral, firmly bonded product was obtained.

The resulting fabric evidenced a 99.4% reduction in bacterial growth on one outer surface and a 99.5% reduction on the other, as compared with a control sample.

EXAMPLE 4

Two 0.00375 inch polyvinyl chloride film elements were laminated to a nylon reinforcing element by means of the same plastisol composition and conditions as was used in Examples 1 and 2, except that no antibacterial agent was present in the plastisol. This control experiment showed only a 42% reduction in bacterial growth on one side of the product and 0% reduction on the opposite side.

EXAMPLE 5

A 0.00375 inch thick sheet of polyvinyl chloride film was coated with a water-based emulsion of polyvinyl chloride, Geon 576, containing about 1.5% by weight of copper-8-quinolinolate based on the weight of Geon 576. The film of the polymer was drawn down on the vinyl film and then dried.

Upon testing, the product showed a 95.5% reduction in bacterial growth on the untreated side, as compared with a control sample.

EXAMPLE 6

A 0.00375 inch thick polyvinyl chloride base sheet was coated with a 100% solids liquid polymer system consisting of Epon 828-triethylenetetramine which is cured in the presence of about 5% of the antibacterial solution used in Example 2, based on the total weight of the laminate. A nylon scrim element was applied as a backing to the polyvinyl chloride base sheet. The liquid polymer system contains no solvent or water as a carrier. A 98.5% reduction in bacterial growth was observed on the outer side of the polyvinyl chloride base sheet and a 98.6% reduction, was observed on the nylon scrim side of the product.

EXAMPLE 7

The same material was prepared as in the preceding Example except that the antibacterial agent was omitted. A 0% reduction in bacterial growth was observed on both sides.

EXAMPLE 8

A sheet of Aclar, a fluoro halocarbon film, and having a thickness of 0.001 inch, was coated with the plastisol composition of Example 1 containing about 5% of the antibacterial solution of Example 2, based upon film weight. After setting of the plastisol, the material was tested and showed an 84% reduction in bacterial growth on the outer side of the Aclar sheet. A 98% reduction in bacterial growth was observed on the plastisol coated side.

EXAMPLE 9

Material was prepared in the same manner as in the preceding Example, except that the antibacterial agent was omitted. A 0% reduction in bacterial growth was observed on the outer side or surface of the Aclar base sheet and only a 10% reduction was observed on the plastisol side.

EXAMPLE 10

A laminated fabric was prepared under the conditions of Example 1 from two sheets of 0.00375 inch polyvinyl chloride film and a woven nylon scrim element using the plastisol of Example 1 as an adhesive, except that 22 parts of tri-butyltin linoleate to 100 parts of plastisol was used as the antibacterial agent. Sufficient plastisol was used to apply about 5% of antibacterial agent based on film weight. An average bacterial growth reduction of 89% is observed on the surfaces of the laminate, when compared with a control sample.

EXAMPLE 11

Material was prepared as in Example 10, except that 13 parts of the same antibacterial solution as was used in Example 2 were employed as the antibacterial agent and the concentration of antibacterial agent was about 3% based on the film weight. An average reduction in bacterial growth of 99% is observed on the surfaces of the laminate, when compared with a control sample.

EXAMPLE 12

An antibacterial material was prepared as in Example 10, except that 2.3 parts of tributyltin monopropylene glycol maleate is employed as the antibacterial agent and the concentration of antibacterial agent was about 0.5% based on the film weight. An average reduction in bacterial growth of 96% is observed on the surfaces of the laminate when compared with a control sample.

EXAMPLE 13

The same material was prepared as in Example 10, except that a combination of 13 parts of the antibacterial solution as was used in Example 2 (about 3% based on film weight) and 2.3 parts of tributyltin sulfosalicylate (about 0.5% based on film weight) are employed as the antibacterial agent. An average reduction in bacterial growth of 99% is observed on the surfaces of the laminate when compared with a control sample.

Samples obtained in this experiment were subjected to wash cycles in a Kenmore Electric washer and to autoclave treatment. Each washing machine cycle involved a ten minute wash and three minute rinse, with the wash temperature being 135°±5° F., and the rinse temperature being 130°±10° F. The autoclave treatment was at 222°±6° F. for three hours at a pressure of 1-5 psi. During the washing cycle, ¾ cup of Ivory Snow was used for each seventeen gallons of water (full capacity). Sufficient specimens for testing were removed after various cycles and the wash/rinse/autoclave cycle treatment was repeated. Samples were tested for reduction in bacterial growth after the following treatment and compared to unwashed samples:

| WASH CYCLES | AUTOCLAVE CYCLES |
|---|---|
| 3 | 1 |
| 6 | 2 |
| 10 | 3 |
| 15 | 4 |
| 20 | 5 |
| 25 | 6 |

The average reduction in bacterial growth remained essentially at 80% of the initial value after 25 wash cycles and six autoclaves.

It is apparent, therefore, that the process and materials of the invention provide an antibacterial effect in fabrics which persists, substantially unimpaired, through repeated wash and autoclaving treatments.

Other chemical and biological activities, such as, pesticidal, and odorous properties may be introduced into polymeric articles in accordance with the present technique.

It will also be apparent from the following series of examples that combinations of antibacterial agents may be selected to impart effective antibacterial activity against a number of different species of organisms. Likewise, it is demonstrated that a single biological agent or combination of such agents may be selected to provide a polymeric article having a combination of antibacterial, antifungal and other activities, such as, pesticidal, repellent, and odorous activities. In an additional important embodiment of the invention, combinations of chemical and physical properties may be imparted to polymeric articles in accordance with the invention. For example, antibacterial, antifungal, odorous and antistatic properties may all be combined in a polymeric substrate, such as, single or multi-ply fabrics to provide highly desirable products for use in hospitals or other environment where such a combination of properties is very advantageous.

EXAMPLES 14 to 59

In the following series of examples, a wide variety of common, commercially available polymer materials were treated in accordance with the invention to impart chemical activity. Special emphasis was placed on the selection of polymers of widely different chemical types to demonstrate the general application of the invention to non-porous polymer substrates. Commercially available species of most of the prominent commercial types of polymers were utilized and found to be satisfactory for the practice of this invention in combination with selected activating agents.

Likewise, a studied effort was made in the following examples to demonstrate the efficacy of this invention when applied to a wide variety of different types of commercially available biologically active agents. Thus, phenolic, metallo-organic, inorganic metal salt, organic sulfur, antibiotic, quaternary amine, carbonyl, carbocyclic and halogenated carbocyclic, and other biologically active compounds were successfully employed in accordance with the invention.

In the following series of examples, the invention was applied to a wide variety of polymer sheet materials of varying construction. The different types of sheet and laminate constructions used in these examples are designated in Table 1.

TABLE 1

| Sheet or Laminate Type | Description of Construction of Sheet or Laminate |
|---|---|
| A | Film/Plastisol Containing Activating Agent/Film |
| B | Film/Volatile Solvent Containing Binder Resin and Activating Agent |
| C | Cloth/Film Containing Activating Agent/Cloth |
| D | Film/Plastisol Containing Activating Agent/Nylon Scrim Film |
| E | Film/Solid Activating Agent (no binder or solvent)/Film |
| F | Film/Liquid Activating Agent (no binder or solvent)/Film |
| G | Film/Film (inactive system) |
| H | Film/Plastisol/Nylon Scrim Film (inactive system) |
| I | Film/Plastisol Containing Activating Agent |

In Table 1, the plastisol referred to is a plastisol composition of polyvinyl chloride resin in plasticizers as given in Example 1. Solutions used were selected from the following compositions:

(1) Solution No. 1

Polyvinyl chloride/nitrile rubber solution in methyl ethyl ketone.

(2) Solution No. 2

Polyamide resin solution in ethyl alcohol (Versamid-711).

(3) Solution No. 3

Acrylic resin solution in ethyl acetate (Monsanto RA-771).

(4) Solution No. 4

Crepe rubber in "VM&P Naphtha".

In the following examples, the substrate materials which have been referenced by Trade Names are described as follows:

| Name | Chemical Description |
|---|---|
| Aclar | Polychlorotrifluoroethylene |
| Tedlar | Polyvinyl fluoride |
| Tuftane | Polyester urethane |
| Kapton | Polybenzimidazole |
| Surlyn A | Partially neutralized copolymer of ethylene and acrylic acid-ionomer resin |
| Mylar | Polyethylene terephthalate |
| Soran | Polyvinylidene chloride |

TABLE 2

| Example No. | Construction Code Coating Solution No. and Substrate Polymer | Inactive Film Thickness (inches) | Nominal % Active Agent Based On Total Weight | Biological Agent | Antibacterial Test Bacterial Species | Antibacterial Test Percent Reduction | Antifungal Inhibition |
|---|---|---|---|---|---|---|---|
| 14 | B-2 Polyvinyl chloride | 0.004 | 0.65 | Dowicide A | S.A. | 89 | High |
| 15 | B-2 Polyethylene | 0.00125 | 2.83 | Dowicide A | S.A. | 49 | Moderate |
| 16 | B-2 Polyethylene | 0.00125 | 0.51 | Dowicide A | — | Not Tested | Moderate |

TABLE 2-continued

| Example No. | Construction Code Coating Solution No. and Substrate Polymer | Inactive Film Thickness (inches) | Nominal % Active Agent Based On Total Weight | Biological Agent | Antibacteral Test Bacterial Species | Antibacteral Test Percent Reduction | Antifungal Inhibition |
|---|---|---|---|---|---|---|---|
| 17 | B-2 Aclor | 0.005 | 0.95 | Metasol 57 | S.A. | (NT) 99.9 | Total |
| 18 | B-2 Cellulose Acetate | 0.002 | 0.23 | Metasol 57 | S.A. | 99.9 | NT |
| 19 | B-2 Cellulose Acetate | 0.002 | 0.58 | Metasol 57 | S.A. | 97.3 | NT |
| 20 | B-2 Tedlar | 0.002 | 0.46 | Arquad S-50 | S.A. | 21 | |
| 21 | B-2 Tedlar | 0.002 | 0.14 | Arquad S-50 | S.A. | 0 | NT |
| 22 | B-2 Tuftane | 0.005 | 0.71 | Arquad S-50 | S.A. | 31 | NT |
| 23 | B-3 Nylon | 0.001 | 0.92 | Captan | S.A. | 90 | High |
| 24 | B-3 Nylon | 0.001 | 0.40 | Captan | S.A. | 98.8 | Moderate |
| 25 | B-3 Polyethylene | 0.00125 | 2.0 | Captan | — | NT | High |
| 26 | B-3 Polyethylene | 0.0125 | 0.49 | Captan | S.A. | 99.7 | NT |
| 27 | B-2 Nylon | 0.001 | 0.16 | TBTSS | S.A. | 99.7 | NT |
| 28 | B-2 Kapton | 0.002 | 0.37 | Mercuric Chloride | S.A. | 99.7 | None |
| 29 | B-2 Mylar | 0.005 | 0.42 | Mercuric Chloride | S.A. | 99.7 | Low |
| 30 | B-2 Mylar | 0.005 | 0.19 | Paraformaldehyde | S.A. | 77.5 | NT |
| 31 | B-1 Surlyn A | 0.002 | 0.61 | Tetracycline HCL | S.A. | 99.7 | NT |
| 32 | B-1 Surlyn A | 0.002 | 0.72 | Tetracycline HCL | S.A. | 99.6 | NT |
| 33 | B-1 Nylon | 0.002 | 0.50 | Tetracycline HCL | S.A. | 99.7 | NT |
| 34 | B-1 Nylon | 0.002 | 0.08 | Tetracycline HCL | S.A. | 99.7 | NT |
| 35 | B-2 Polyethylene | 0.00125 | 0.66 | TBTSS | S.A. | 99.4 | NT |
| 36 | B-2 Polyethylene | 0.00125 | 0.37 | TBTSS | S.A. | 87.1 | NT |
| 37 | B-2 Tuftane | 0.005 | 4.0 | Arquad S-50 | S.A. | 96.5 | NT |
| 38 | B-2 Polyethylene | 0.00125 | 3.0 | Arquad S-50 | S.A. | 0 | NT |
| 39 | B-2 Polyvinyl Chloride | 0.008 | 4.0 | Dowicide A | S.A. | 0 | Total |
| 40 | B-2 Mylar | 0.005 | 3.0 | Paraformaldehyde | S.A. | 86.8 | NT |
| 41 | B-2 Saran | 0.002 | 2.0 | Mercuric Chloride | S.A. | 90 | — |
| 42 | B-3 Tedlar | 0.002 | 3.0 | Captan | S.A. | 62 | Low |
| 43 | B-2 Polyethylene | 0.002 | 0.1 | BioMeT 14 | S.A | 0 | NT |
| 44 | B-2 Polyethylene | 0.002 | 1.0 | BioMeT 14 | S.A. | 27 | None |
| 45 | B-1 Polyvinyl Chloride | 0.004 | 0.5 | Hexachlorophene | S.A. | 42.5 (1) | Moderate |
| 46 | B-1 Polyvinyl Chloride | 0.004 | 3.0 | Hexachlorophene | S.A. | 52.6 (1) | Moderate |
| 47 | B-2 Polyvinyl Chloride | 0.004 | 3.0 | Hyamine 1622 | S.A. | 91.9 (1) | NT |
| 48 | B-2 Polyvinyl Chloride | 0.004 | 3.0 | Hyamine 3500 | S.A. | 86.9 (1) | NT |
| 49 | B-2 Polyvinyl Chloride | 0.004 | 1.0 | Metasol BT | S.A. | 99.9 | Total |
| 50 | B-1 Polyvinyl Chloride | 0.004 | 2.0 | Fungitrol II | — | NT | High |
| 51 | B-3 Polypropylene | 0.00125 | 1.0 | Captan | S.A. | 37 | Low |
| 52 | B-2 Polypropylene | 0.005 | 1.0 | Metasol 57 | S.A. | 99.4 | Total |
| 53 | E Polyvinyl Chloride | 0.0034/0.0034 | 3.0 | Captan | S.A. | 99.9 | |
| 54 | G Polyvinyl Chloride | 0.0034/0.0034 | None | None | S.A. | 0 | NT |
| 55 | D Polyvinyl Chloride | 0.0034/ | 0.21 | BioMeT 14 | S.A. E.C. P.A. | 99.9 99.9 99.7 | NT |
| 56 | D Polyvinyl Chloride | 0.0034/0.0034 | 0.33 | Captan | S.A. E.C. P.A. | 99.9 92.4 50.5 | NT |
| 57 | D Polyvinyl Chloride | 0.0034/0.0034 | 0.01 0.30 | BioMeT 14 & Captan | S.A. E.C. P.A. | 99.9 82.3 86.6 | NT |
| 58 | D Polyvinyl Chloride | 0.004/0.0034 | 0.30 | Captan | S.A. B.A. E.C. P.M. | 1.0 mm 6.0 mm 0.5 mm (2) 0.5 mm | NT |
| 59 | B-4 Crepe Rubber | 0.008 | 1.0 | Metasol BT | S.A. | 98.9 | NT |

NOTES:
(1) NYS-63 Modified Test
(2) Modified Agar Plate Method—Results By Zone of Inhibition

EXAMPLES 60-68

A series of laminated materials were prepared by laminating a polymer film to a sheet of cotton fabric using an aqueous rubber latex adhesive binder containing 6% (by weight of the adhesive binder) of a pesticide. The latex utilized was "Hycar-1552" and the pesticide was "Pyronyl 101", an emulsion concentrate of 1.2% pyrethrins and 12.0% piperonyl butoxide. The laminates were tested with corn meal with the polymer film side of the laminate facing the grain. After two weeks, the corn meal was tested for pesticide to determine the extent of migration of the pesticide from the aqueous rubber latex binder through the polymer film and into the corn meal. The results reported in the following table indicate that significant pesticidal migration took place in each instance.

TABLE 3

| Example No. | Film Type | Thickness (inches) | Pesticide/mg/ft² In the Active Layer | % Pesticide Determined (1) After Two Weeks Accelerated Exposure | |
|---|---|---|---|---|---|
| | | | | In Film Fabric | Transmitted Through Film To Corn Meal |
| 60 | Cellophane | 0.001 | 28.2 | 91 | 9 |
| 61 | Lexan (polycarbonate) | 0.002 | 17.5 | 78 | 22 |
| 62 | Polyester Kodar | 0.002 | 12.5 | 76 | 24 |
| 63 | Mylar | 0.001 | 47.5 | 96 | 4 |
| 64 | Polyamide | 0.001 | 57.7 | 96 | 4 |
| 65 | Vinyl | 0.002 | 20.0 | 81 | 19 |
| 66 | Polyethylene | 0.001 | 47.5 | 67 | 33 |
| 67 | Lexan | 0.002 | 45.0 | 91 | 9 |
| 68 | Polyester Kodar | 0.002 | 60.5 | 96 | 4 |

Note:
(1) Quantitative analysis of pesticide was performed colorimetrically.

EXAMPLES 69–70

The invention also showed utility in the production of nonporous, polymeric articles having active odorous properties, as shown in the following examples.

EXAMPLE 69

A laminate of two 0.004 inch thick films of polyvinyl chloride was formed incorporating a nylon scrim reinforcing element and using a plastisol adhesive incorporating 0.5% by weight of the laminate of a synthetic leather essence. Immediately after the laminate was formed, it was confirmed by a smell test of the resulting product that a distinct leather-like odor had been imparted to the product.

EXAMPLE 70

Example 69 was repeated except for the substitution of a synthetic rose essence for the leather essence and the use of 0.00875 and 0.0055 inch thick plies of polyvinyl chloride. Immediately after the laminate was formed, the smell test confirmed the presence of a distinct rose-like odor emanating from the outer surface of the laminate.

EXAMPLES 71–73

One of the preferred embodiments of this invention includes the use of a textile fabric which has been activated by contact with an active layer by migration of the active ingredient into the body of the fibers of the cloth. This effect is independent of the porosity of the fabric, and in fact is not related to the porosity. It has been shown in the prior art that porous substrates may be activated by means of an adhesive containing an active agent introduced between layers of porous material. Examples 71 through 73 demonstrate that it is not necessary that porosity exist in a textile fabric, since, according to this invention, the yarns or fibers themselves may be made to take up the active agent by migration. The advantage of this is that the active ingredient is not easily washed out by laundering, but becomes an integral part of the substrate yarns. As with other products of this invention, active properties on the surfaces of the fibers are continuously replenished from the reservoir of active agent within the active layer.

EXAMPLE 71

A fabric was prepared by placing a cotton woven cloth having a thickness of about 0.015 inch in contact with an active film of polyvinyl chloride containing the antibacterial agent, captan. The captan was present in an amount to provice 0.53% of the active agent based on the total weight of the composite.

The side of the cloth not in contact with the active film was then tested by the modified Agar Plate Method for antibacterial activity against S. Aureus. The uncontacted side of the cotton cloth exhibited an effective level of antibacterial activity as it was observed to provide a 2.75 mm. zone of inhibition.

EXAMPLE 72

A sample was prepared by placing a completely desized cotton textile, 0.012 inch thick, against an active film 0.0055 inch thick and containing 3.0% of Metasol BT, based on the total weight of the laminate, under a pressure of 3.3 psi for 96 hours and allowing the active agent to migrate into the fibers of the textile. The textile was then separated from the active film and the side which had been out of contact with the active film was tested by the NYS-63 Method for activity against S. Aureus. A 99.9% reduction in bacterial growth was observed.

EXAMPLE 73

A 1¼" circle of completely desized cotton fabric was coated around its periphery with a plastisol containing 3.0% of Metasol BT based on the total weight of the sample. The plastisol was hardened by fusing for five minutes at 350° F. and cooling. After 96 hours, at room temperature, only the uncoated center of the disc of cotton fabric was cut out and tested for activity against S. Aureus by the NYS-63 Method. A 99.9% reduction in bacterial growth was observed.

EXAMPLES 74–75

The application of the invention in the production of polymeric articles having active insecticidal or animal repellent properties is demonstrated in the following examples.

EXAMPLE 74

A laminate of construction B, incorporating a Saran film 0.00075 inch thick, and coating No. 2 containing 1.8% of "Chlordane" was observed by scanning electron microscopy. Effective migration was evidenced by the presence of crystals of the active agent, "Chlordane", on the uncoated surface of the material.

EXAMPLE 75

A laminate of construction B, incorporating a Mylar film 0.00075 inch thick and coating No. 3 containing 2.2% of methyl nonyl ketone was tested as in Example 74 and gave positive evidence of effective migration of the active agent.

Other examples of the application of the invention to the production of antibacterial materials are set forth below.

EXAMPLE 76

(A) A first, integral multi-ply material was produced by laminating together two plies of polyvinyl chloride incorporating 0.4% (by weight based upon the total weight of the laminate) of the active antibacterial agent bis(tri-n-butyltin)sulfosalicylate (the antibacterial agent disclosed in U.S. Pat. No. 3,279,986). A layer of plastisol adhesive was employed to assist the bonding of the plies, and a nylon reinforcing fabric or scrim was introduced as a core layer and was sandwiched between the polyvinyl chloride plies.

In this example, surfaces of the laminate were tested for antibacterial activity against S. Aureus.

The outer surface of one of the outer plies of polyvinyl chloride was tested for antibacterial activity by the "Agar Plate Method" and showed a 0.2 mm. zone of inhibition.

The surfaces of a discrete, untreated film of polyvinyl chloride were then tested for antibacterial activity by the same method and showed no antibacterial activity, i.e., no zone inhibition.

The discrete, untreated film of polyvinyl chloride was then laminated to the previously tested outer surface of one of the polyvinyl chloride plies of the first laminate to form a second laminated product. The second laminate was then tested to determine antibacterial activity on the outer surface of the untreated polyvinyl chloride film, but no activity, i.e., no zone inhibition was found.

(B) The above procedure (A) was followed except for the following variations:

(1) The polyvinyl chloride plies of the first laminate contain no antibacterial agent;

(2) The plastisol had incorporated therein 0.3% (by weight, based upon the total weight of the laminate) of the active antibacterial agent N-[(trichloromethyl)thio]-4-cyclohexene-1,2-dicarboxamide.

One of the outer surfaces of the first laminate was tested for antibacterial activity and showed a 4.8 mm. zone of inhibition. The discrete, untreated film again showed no zone of inhibition prior to lamination.

Upon lamination of the untreated polyvinyl chloride to form the second laminate, however, the outer surface of the untreated film showed antibacterial activity by a 3.5 mm. zone of inhibition.

The foregoing example demonstrates that the phenomenon of this invention is not inherent in the lamination of one polymer film to a pretreated polymer film, but depends upon the proper selection and combination of polymers and active agents.

EXAMPLES 77–87

An integral multi-ply material was formed of two plies of polyvinyl chloride containing no antibacterial agent, a plastisol adhesive layer containing an amount and type of antibacterial agent as set forth in Table 4 below and a nylon reinforcing core layer.

Table 4 sets forth the identity and amount of antibacterial agent present in the plastisol adhesive layer (in percent by weight, based upon the total weight of the laminate) and the results of testing for antibacterial activity of the outer surfaces against S. Aureus. The test for antibacterial activity employed is the NYS-63 Method.

EXAMPLES 88–89

Examples were prepared according to construction I using 0.004 inch thick polyvinyl chloride film and TBTSS as the activating agent in the plastisol. The samples were tested for antibacterial activity on the uncoated side against S. Aureus using the NYS-63 Method. The results are reported in Table 4.

TABLE 4

| Ex. No. | Antibacterial Agent | Concentration % Based on Film Weight | Per Cent Reduction of Bacteria | |
|---|---|---|---|---|
| | | | Side 1 | Side 2 |
| 77 | none | — | 44.2 | 50.6 |
| 78 | tributyltin neodecanoate | 5.0 | 98.0 | 95.4 |
| 79 | tributyltin linoleate | 5.0 | 92.4 | 87.7 |
| 80 | 10,10'-oxybisphenoxyarsine | 5.0 | 99.2 | 99.9 |
| 81 | tributyltin neodecanoate | 0.5 | 60.3 | 55.1 |
| 82 | tributyltin linoleate | 0.5 | 60.2 | 52.8 |
| 83 | tributyltin monopropyleneglycol maleate | 0.5 | 95.6 | 95.9 |
| 84 | 10,10'-oxybisphenoxyarsine | 0.5 | 99.2 | 99.6 |
| 85 | tributyltin acetate | 0.5 | 0 | 32.9 |
| 86 | 10,10'-oxybisphenoxyarsine | 3.0 | 99.9 | 99.7 |
| 87 | TBTSS | 0.5 | 49.4 | 38.1 |
| 88 | TBTSS | 0.5 | 59 | — |
| 89 | TBTSS | 5.0 | 26 | — |

EXAMPLES 90–97

In another important embodiment, special physical properties may be imparted to polymeric articles in accordance with the invention. For example, antistatic and electrically conductive properties may be incorporated into a polymeric article by the present method.

Application of the invention to impart physical activity to polymeric materials are set forth in the examples which are reported in Table 5. In the examples, "Volume Resistivity" was tested by Test Method NFPA No. 56A, para. 2541 and 25433(3), and "Surface Resistivity" was tested by Test Method NFPA No. 56A, para. 25433(3) [AATCC 76-59 Method]. The foregoing are used to determine the electrical conductivity of the tested materials. Antistatic materials have a sufficiently high electrical conductivity to dissipate electrostatic charges which may be generated on their surfaces.

TABLE 5

| Example No. | Construction Code Coating Solution No. and Substrate Polymer | Film Thickness (inches) | Nominal % Active Agent Based On Total Weight | Antistatic Agent | Volume Resistivity (ohms) | Surface Resistivity ohms square |
|---|---|---|---|---|---|---|
| 90 | H Polyvinyl Chloride | 0.004/0.0034 | none | none | $1 \times 10^7$ | — |
| 91 | D Polyvinyl Chloride | 0.004/0.0034 | 1.0 | Advastat 50 | $3 \times 10^5$ | — |
| 92 | D Polyvinyl Chloride | 0.004/0.0034 | 1.2 | Aston 123 | $5.4 \times 10^6$ | — |

TABLE 5-continued

| Example No. | Construction Code Coating Solution No. and Substrate Polymer | Film Thickness (inches) | Nominal % Active Agent Based On Total Weight | Antistatic Agent | Volume Resistivity (ohms) | Surface Resisitivity ohms square |
|---|---|---|---|---|---|---|
| 93 | G Polyvinyl Chloride | 0.0034/0.0034 | none | none | $4.7 \times 10^7$ | — |
| 94 | F Polyvinyl Chloride | 0.0034/0.0034 | 11.2 | Advastat 50 | $1.9 \times 10^5$ | — |
| 95 | A Polyvinyl Chloride | 0.0034/0.0034 | 3.0 | Advastat 50 | $3.5 \times 10^5$ | — |
| 96 | H Polyvinyl Chloride | 0.00375/0.00375 | none | none | — | $7.5 \times 3$ |
| 97 | D Polyvinyl Chloride | 0.00375/0.00375 | 9.6 | Nafton-AT | — | $8 \times 10$ |

EXAMPLE 98

A multi-layer material was prepared by coating one surface of a polyvinyl chloride film, 0.0034 inches thick, with a liquid antistatic activating agent consisting 11.2% Advastat 50 (based on the total weight of the laminate) and laminating a second polyvinyl chloride film, 0.0034 inches thick, so as to encapsulate the Advastat 50 between the plies. A second, similar, laminate was made except that no active layer was used. The electrical conductivity of each laminate was measured after 48 hours at room temperature. The volume resistivity of the first laminate, containing the active agent, was $5.5 \times 10^5$ ohms, and of the second laminate, with no activating agent, was $3.5 \times 10^8$ ohms. The plies of the first laminate were subsequently separated and the activating agent was completely washed off. The plies were recombined as before, but without activating agent, and the volume resistivity was measured and found to be $5.0 \times 10^5$ ohms.

EXAMPLE 99

Two layers of fiber glass fabric, Style 181/150, Volan, were impregnated with a fire resistant unsaturated thermosetting polyester compound and combined and hardened with an organic peroxide under heat and pressure to a total thickness of 0.017 inches. A plastisol composition containing Metasol BT at a concentration of 3% by weight of the final laminate was applied to one surface of the polyester/fiber glass layer and hardened at 300° F. for four minutes. The unactivated surface was tested by the NYS-63 Method and effective inhibition of S. Aureus bacteria was observed.

In an additional important embodiment of the invention, combinations of chemical and physical properties may be imparted to polymeric articles in accordance with the invention. For example, antibacterial, antifungal, odorous and antistatic properties may all be combined in a polymeric substrate, such as, single or multiply fabrics to provide highly desirable products for use in hospitals or other environment where such a combination of properties is extremely important. For example, a very useful laminate is provided by bonding two outer plies of 0.004 and 0.00375 inch polyvinyl chloride film to a nylon scrim reinforcing core element by use of a plastisol adhesive containing both Captan and Advastat 50 to impart a combination of antibacterial and antistatic properties to the outer surfaces of the product.

What is claimed is:

1. A method for producing a polymeric article having active properties comprising antibacterial, antifungal and combinations thereof comprising adherently applying to at least one surface of a preformed, solid, non-porous polymeric substrate an adherent, solid, non-porous layer of a polymeric composition, said composition comprising at least one non-volatile active agent selected from the group consisting of antibacterial, antifungal and combinations of antibacterial and antifungal active agents distributed within said polymeric composition and capable of migrating from said layer into and throughout said substrate, and maintaining said layer adhered to said surface of said substrate to permit a sufficient amount of said active agent to migrate from said layer into said substrate to impart an effective level of activity throughout said substrate, including a surface of said substrate which is not directly contacted by said layer.

2. A method for producing a polymeric article having active antibacterial properties comprising adherently applying to at least one surface of a preformed, solid non-porous polymeric substrate an adherent, solid, non-porous layer of a polymeric composition, said composition comprising at least one non-volatile antibacterially active agent distributed within said polymeric composition and capable of migrating from said layer into and throughout said substrate, and maintaining said layer adhered to said surface of said substrate to permit a sufficient amount of said antibacterially active agent to migrate from said layer into said substrate to impart an effective level of antibacterial activity throughout said substrate, including a surface of said substrate which is not directly contacted by said layer.

3. The method of claim 2 wherein said antibacterially active agent comprises one or more materials selected from the group consisting of phenolic, metallo-organic, inorganic metal salt, organic sulfur, antibiotic, quaternary organic salt, carbonyl, carbocyclic compounds having a carbonyl group, and halogenated carbocyclic compounds.

4. The method of claim 2 wherein said substrate is a material selected from the group consisting of a lower polyolefin, polyvinyl chloride, polyvinyl fluoride, polychlorotrifluoroethylene, polyester, urethane, polycarbonate, polyethylene terephthalate, polyvinylidene chloride, polybenzimidazole, ethylene-acrylic acid copolymer ionomer, cellulose acetate, regenerated cellulose, polyamide and cotton.

5. The method of claim 2 further comprising the step of bonding a second material to said layer on the surface not contacted by said substrate.

6. The method of claim 2 wherein said second material is selected from the group consisting of metal, wood, plastic, particle board, paper, textile, asbestos, multilayer laminated elements, and elements which serve as a barrier to said antibacterially active agent.

7. The method of claim 2 further comprising stripping said layer from said substrate after said effective level of antibacterial activity has been imparted throughout said substrate, including a surface of the substrate not contacted by said layer.

8. A method for producing a polymeric article having active antifungal properties comprising adherently applying to at least one surface of a preformed, solid, non-porous polymeric substrate an adherent, solid, non-porous layer of a polymeric composition, said composition comprising at least one non-volatile antifungally active agent distributed within said polymeric composition and capable of migrating from said layer into and throughout said substrate, and maintaining said layer adhered to said surface of said substrate to permit a sufficient amount of said antifungally active agent to migrate from said layer into said substrate to impart an effective level of antifungal activity throughout said substrate, including a surface of said substrate which is not directly contacted by said layer.

9. The method of claim 8 wherein said antifungally active agent comprises one or more materials selected from the group consisting of phenolic, metallo-organic, inorganic metal salt, organic sulfur, antibiotic, quaternary organic salt, carbonyl, carbocyclic compounds having a carbonyl group, and halogenated carbocyclic compounds.

10. The method of claim 8 wherein said substrate is a material selected from the group consisting of a lower polyolefin, polyvinyl chloride, polyvinyl fluoride, polychlorotrifluoroethylene, polyester, urethane polycarbonate, polyethylene terephthalate, polyvinylidene chloride, polybenzimidazole, ethylene-acrylic acid copolymer ionomer, cellulose acetate, regenerated cellulose, polyamide and cotton.

11. The method of claim 8 further comprising the step of bonding a second material to said layer on the surface not contacted by said substrate.

12. The method of claim 11 wherein said second material is selected from the group consisting of metal, wood, plastic, particle board, paper, textile, asbestos, multilayer laminated elements, and elements which serve as a barrier to said antifungally active agent.

13. The method of claim 8 further comprising stripping said layer from said substrate after said effective level of antifungal activity has been imparted throughout said substrate, including a surface of the substrate not contacted by said layer.

14. A method for producing a polymeric article having a combination of active antibacterial and antifungal properties comprising adherently applying to at least one surface of a preformed, solid, non-porous polymeric substrate an adherent, solid, non-porous layer of a polymeric composition, said composition comprising at least one non-volatile antibacterially active agent and at least one non-volatile antifungally active agent distributed within said polymeric composition and capable of migrating from said layer into and throughout said substrate, and maintaining said layer adhered to said surface of said substrate to permit a sufficient amount of said active agents to migrate from said layer into said substrate to impart an effective level of antibacterial and antifungal activity throughout said substrate, including a surface of said substrate which is not directly contacted by said layer.

15. The method of claim 14 wherein said antibacterially and antifungally active agents comprise one or more materials selected from the group consisting of phenolic, metallo-organic, inorganic metal salt, organic sulfur, antibiotic, quaternary organic salt, carbonyl, carbocyclic compounds having a carbonyl group, and halogenated carbocyclic compounds.

16. The method of claim 14 wherein said substrate is a material selected from the group consisting of a lower polyolefin, polyvinyl chloride, polyvinyl fluoride, polychlorotrifluoroethylene, polyester, urethane, polycarbonate, polyethylene terephthalate, polyvinylidene chloride, polybenzimidazole, ethylene-acrylic acid copolymer ionomer, cellulose acetate, regenerated cellulose, polyamide and cotton.

17. The method of claim 14 further comprising the step of bonding a second material to said layer on the surface not in contact with said substrate.

18. The method of claim 17 wherein said second material is selected from the group consisting of metal, wood, plastic, particle board, paper, textile, asbestos, multilayer laminated elements, and elements which serve as a barrier to said activating agent.

19. The method of claim 14 further comprising stripping said layer from said substrate after said effective levels of antibacterial and antifungal activity have been imparted throughout said substrate, including a surface of the substrate not contacted by said layer.

20. A method for producing a polymeric article having active biological properties comprising adherently applying to at least one surface of a preformed, solid, non-porous, polymeric substrate an adherent layer of a polymeric composition, said composition comprising at least one non-volatile biologically active agent capable of migrating from said layer into and throughout said substrate, and maintaining said layer adhered to said surface of said substrate to permit a sufficient amount of said biologically active agent to migrate from said layer into said substrate to impart an effective level of biological activity throughout said substrate, including a surface of said substrate which is not directly contacted by said layer.

21. A method for producing a polymeric article having active pesticidal properties comprising adherently applying to at least one surface of a preformed, solid, non-porous, polymeric substrate an adherent layer of a polymeric composition, said composition comprising at least one non-volatile pesticidally active agent capable of migrating from said layer into and throughout said substrate, and maintaining said layer adhered to said surface of said substrate to permit a sufficient amount of said pesticidally active agent to migrate from said layer into said substrate to impart an effective level of pesticidal activity throughout said substrate, including a surface of said substrate which is not directly contacted by said layer.

22. The method of claim 21 wherein said pesticidally active agent is an antibacterially active agent.

23. The method of claim 21 wherein said pesticidally active agent is an antifungally active agent.

24. The method of claim 21 wherein said pesticidally active agent is an insecticidally active agent.

25. The method of claim 21 wherein said pesticidally active agent is a pest repellent active agent.

26. The method of claim 21 wherein said pesticidally active agent comprises a phenolic compound.

27. The method of claim 21 wherein said pesticidally active agent comprises a metallo-organic compound.

28. The method of claim 21 wherein said pesticidally active agent comprises an inorganic metal salt compound.

29. The method of claim 21 wherein said pesticidally active agent comprises an organic sulfur compound.

30. The method of claim 21 wherein said pesticidally active agent comprises an antibiotic material.

31. The method of claim 21 wherein said pesticidally active agent comprises a quaternary organic salt compound.

32. The method of claim 21 wherein said pesticidally active agent comprises a carbonyl compound.

33. The method of claim 21 wherein said pesticidally active agent comprises a carbocyclic compound having a carbonyl group.

34. The method of claim 21 wherein said pesticidally active agent comprises a halogenated carbocyclic compound.

35. A method for producing a polymeric article having active physical properties comprising
adherently applying to at least one surface of a preformed, solid, non-porous, polymeric substrate an adherent layer of a polymeric composition, said composition comprising at least one non-volatile physically active agent capable of migrating from said layer into and throughout said substrate, and
maintaining said layer adhered to said surface of said substrate to permit a sufficient amount of said physically active agent to migrate from said layer into said substrate to impart an effective level of physical activity throughout said substrate, including a surface of said substrate which is not directly contacted by said layer.

36. A method for producing a polymeric article having active antistatic properties comprising
adherently applying to at least one surface of a preformed, solid, non-porous, polymeric substrate an adherent layer of a polymeric composition, said composition comprising at least one non-volatile antistatically active agent capable of migrating from said layer into and throughout said substrate and
maintaining said layer adhered to said surface of said substrate to permit a sufficient amount of said antistatically active agent to migrate from said layer into said substrate to impart an effective level of antistatic activity throughout said substrate, including a surface of said substrate which is not directly contacted by said layer.

37. A method for producing a polymeric article having active electrically conducting properties comprising
adherently applying to at least one surface of a preformed, solid, non-porous, polymeric substrate an adherent layer of a polymeric composition, said composition comprising at least one active non-volatile electrically conductive agent capable of migrating from said layer into and throughout said substrate, and
maintaining said layer adhered to said surface of said substrate to permit a sufficient amount of said active electrically conductive agent to migrate from said layer into said substrate to impart an effective level of electrical conductivity throughout said substrate, including a surface of said substrate which is not directly contacted by said layer.

* * * * *